United States Patent
Pandey et al.

(10) Patent No.: US 11,417,439 B2
(45) Date of Patent: Aug. 16, 2022

(54) RAPID ISOLATION OF CYCLOTRON-PRODUCED GALLIUM-68

(71) Applicant: Mayo Foundation for Medical Education and Research, Rochester, MN (US)

(72) Inventors: Mukesh K. Pandey, Rochester, MN (US); Timothy R. DeGrado, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 844 days.

(21) Appl. No.: 16/328,171

(22) PCT Filed: Aug. 28, 2017

(86) PCT No.: PCT/US2017/048823
§ 371 (c)(1),
(2) Date: Feb. 25, 2019

(87) PCT Pub. No.: WO2018/039662
PCT Pub. Date: Mar. 1, 2018

(65) Prior Publication Data
US 2019/0198187 A1  Jun. 27, 2019

Related U.S. Application Data

(60) Provisional application No. 62/380,183, filed on Aug. 26, 2016.

(51) Int. Cl.
*G21G 1/10*   (2006.01)
*G21G 1/00*   (2006.01)
(Continued)

(52) U.S. Cl.
CPC ............. *G21G 1/001* (2013.01); *C01G 9/00* (2013.01); *C01G 15/00* (2013.01); *C07B 59/00* (2013.01);
(Continued)

(58) Field of Classification Search
CPC ............ G21G 1/001; G21G 1/10; G21G 4/08; G21G 2001/0021; G21G 2001/0094;
(Continued)

(56) References Cited

U.S. PATENT DOCUMENTS

2007/0031329 A1   2/2007   Velikyan et al.
2013/0055855 A1   3/2013   Le
2017/0221594 A1*  8/2017   DeGrado ............... G21G 1/001

FOREIGN PATENT DOCUMENTS

WO   2015/175972 A2   11/2015
WO   2016197084 A1    12/2016

OTHER PUBLICATIONS

Kasbollah, A. (2013) Zirconium-89 for positron emission tomography and hydroxamate resin column for gallium-68 generator, Doctor of Philosophy (PhD), Medical Sciences, RMIT University.
(Continued)

*Primary Examiner* — Jack W Keith
*Assistant Examiner* — Daniel Wasil
(74) *Attorney, Agent, or Firm* — Quarles & Brady LLP

(57) ABSTRACT

Methods for rapid isolation of radionuclides (e.g., $^{68}$Ga) produced using a cyclotron and methods for recycling of the parent isotope (e.g., $^{68}$Zn) are disclosed. In one version of the method, a solution including a radionuclide (e.g., $^{68}$Ga) is created from a target including cations (e.g., $^{68}$Zn). The solution including the radionuclide is passed through a first column including a sorbent comprising a hydroxamate resin to adsorb the radionuclide on the sorbent, and the radionuclide is eluted off the sorbent. The cations (e.g., $^{68}$Zn) are
(Continued)

recovered from a recovery solution that has passed through the first column by passing the recovery solution through a second column including a second sorbent comprising a cation exchange resin.

20 Claims, 1 Drawing Sheet

(51) Int. Cl.
| | |
|---|---|
| *C07B 59/00* | (2006.01) |
| *C01G 9/00* | (2006.01) |
| *C01G 15/00* | (2006.01) |
| *G21G 4/08* | (2006.01) |
| *A61K 51/06* | (2006.01) |

(52) U.S. Cl.
CPC ............... *G21G 1/10* (2013.01); *G21G 4/08* (2013.01); *A61K 51/06* (2013.01); *C01P 2006/44* (2013.01); *G21G 2001/0021* (2013.01); *G21G 2001/0094* (2013.01)

(58) Field of Classification Search
CPC .......... C01G 9/00; C01G 15/00; C07B 59/00; A61K 51/06; C01P 2006/44
USPC .......................................................... 376/195
See application file for complete search history.

(56) References Cited

OTHER PUBLICATIONS

Banerjee SR, et al., Clinical applications of Gallium-68. Appl Radiat Isot 2013; 76: 2-13.
Baum RP, et al., Theranostics: from molecular imaging using Ga-68 labeled tracers and PET/CT to personalized radionuclide therapy-the Bad Berka experience. Theranostics 2012; 2: 437-47.
Belosi F, et al., Generator breakthrough and radionuclidic purification in automated synthesis of 68Ga-DOTANOC. Curr Radiopharm 2013, 6: 72-7.
Dias, Gemma, et al. "Peptide radiolabeling using 68Ga directly produced in liquid targets: development of an improved purification method." Journal of Nuclear Medicine 57.supplement 2 (2016): 381-381.
Engle JW, et al., Very high specific activity 66/68Ga from zinc targets for PET. Appl Radiat Isot 2012; 70: 1792-1796.
Hofman MS, et al., High management impact of Ga-68 DOTATATE (GaTate) PET/CT for imaging neuro-endocrine and other somatostatin expressing tumours. J Med Imaging Radiat Oncol 2012; 56:40-7.
Jacobsson H, et al., Normal uptake of 68Ga-DOTA-TOC by the pancreas uncinate process mimicking malignancy at somatostatin receptor PET. Clin Nucl Med 2012; 37: 362-5.
Jensen M, et al., Direct production of Ga-68 from proton bombardment of concentrated aqueous solutions of [Zn-68] zinc chloride. Proceedings of 13th International Workshop on Targetry and Target Chemistry 2011; 288-292.
Öberg K., Gallium-68 somatostatin receptor PET/CT: Is it time to replace 111Indium DTPA octreotide for patients with neuroendocrine tumors? Endocrine 2012; 42: 3-4.
Rosch F., Past, present and future of 68Ge/68Ga generators. Appl Radiat Isot 2013; 76: 24-30.
Sadeghi M, et al., Determination of 68Ga production parameters by different reactions using ALICE and TALYS codes. Pramana J Phys 2009; 72: 335-341.
Schreiter NF, et al., Cost comparison of 111In-DTPA-octreotide scintigraphy and 68Ga-DOTATOC PET/CT for staging enteropancreatic neuroendocrine tumours. Eur J Nucl Med Mol Imaging 2012; 39: 72-82.
Smith DL, et al., The untapped potential of Gallium 68-PET: Thenext wave of 68Ga-agents. Appl Radiat Isot 2013; 76: 14-23.
Velikyan I., Prospective of 68Ga-Radiopharmaceutical Development. Theranostics 2014; 4:47-80.
Zimmerman BE., Current status and future needs for standards of radionuclides used in positron emission tomography. Appl Radiat Isot 2013; 76: 31-37.
International Search Report and Written Opinion from Parent PCT/US17/48823, dated Nov. 9, 2017, 13 pages.
Pandey, et al., Cyclotron production of 68Ga via the 68Zn(p,n)68Ga reaction in aqueous solution, Am J Nucl Med Mol Imaging, 2014; 4(4):303-310.
Holland, et al., Standardized methods for the production of high specific-activity zirconium-89, Nucl Med Biol 2009; 36(7):729-739.
Miller, et al., Understanding ion-exchange resins for water treatment systems, Apr. 16, 1981, p. 6.
Wikipedia "Ion chromatography" Aug. 18, 2016 (Aug. 18, 2016) p. 5, para. 6-7.
BIO-RAD "Safety Data Sheet" Jun. 16, 2015 (Jun. 16, 2015) p. 1, Section 1; p. 2, Section 3.
Pandey, et al., Improved production and processing of 89Zr using a solution target, Nuclear Medicine and Biology 43 (2016) 97-100.
Sadeghi, et al., Cyclotron production of 68Ga via proton-induced reaction on 68Zn target, NUKLEONIKA 2009,54 (1):25-28.

* cited by examiner

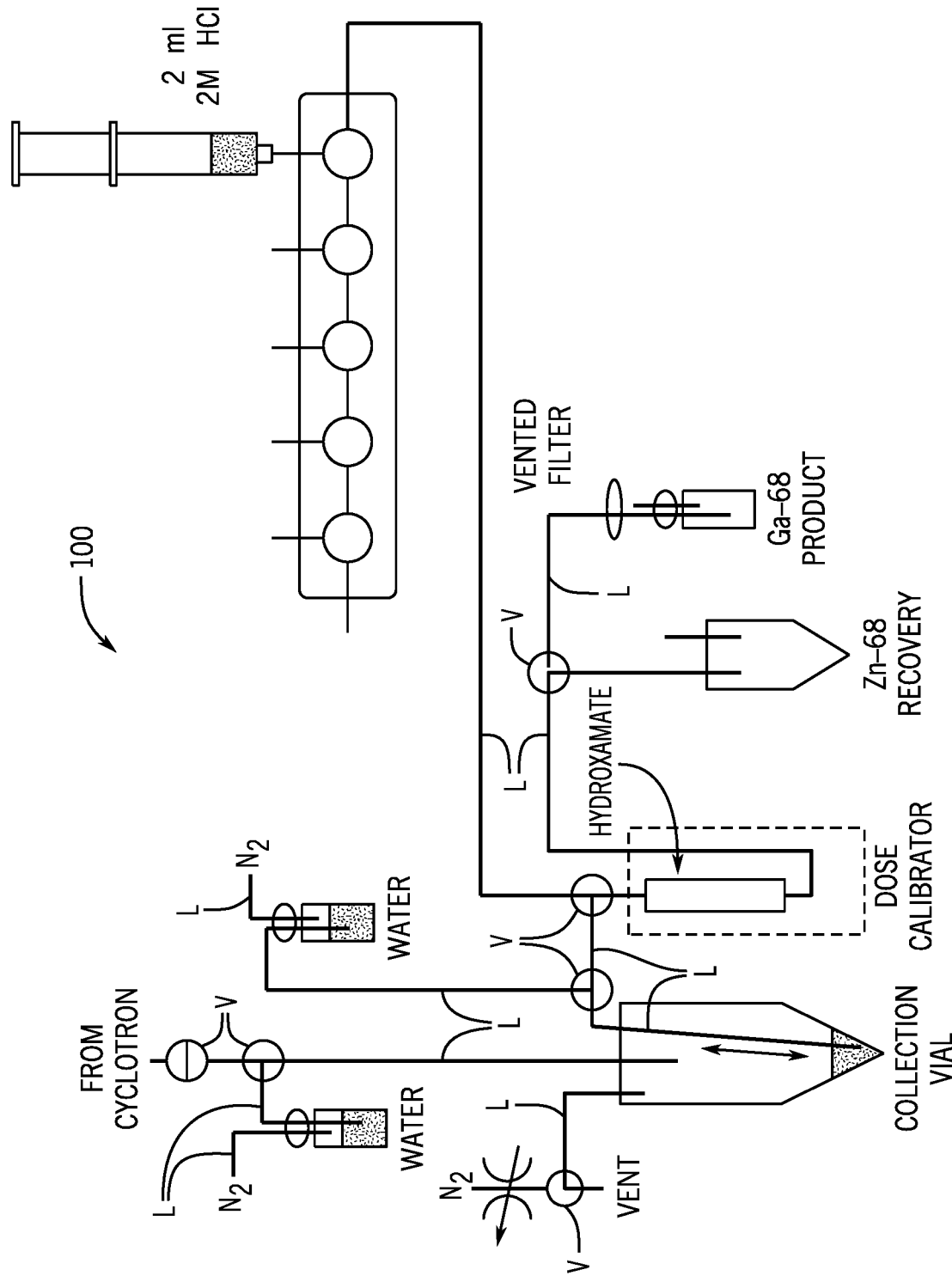

RAPID ISOLATION OF CYCLOTRON-PRODUCED GALLIUM-68

CROSS-REFERENCE TO RELATED APPLICATIONS

This application is a U.S. 371 national phase application of PCT/US17/48823, filed Aug. 28, 2017, which claims priority from U.S. Patent Application No. 62/380,183 filed Aug. 26, 2016.

STATEMENT REGARDING FEDERALLY SPONSORED RESEARCH

This invention was made with government support under DE-SC0008947 awarded by the Department of Energy. The government has certain rights in the invention.

BACKGROUND OF THE INVENTION

1. Field of the Invention

The present invention relates to labeled radiopharmaceuticals. In particular, the invention relates to improved methods and systems for rapid isolation of radionuclides produced using a cyclotron.

2. Description of the Related Art

Radiometals (e.g., $^{64}$Cu, $^{89}$Zr, $^{67}$Ga, $^{68}$Ga, $^{86}$Y and $^{99m}$Tc) play a pivotal role in nuclear medicine as therapeutic and imaging agents for radiation therapy and labeling of biologically important macromolecules like proteins, peptides and antibodies.

In the recent past, a rapid increase has been noted in both clinical and preclinical studies involving $^{68}$Ga-labeled radiopharmaceuticals [Ref. 1-5]. This increase can be attributed to the favorable physical characteristics of $^{68}$Ga ($E_{\beta max}$ 1.8 MeV, $\beta^+$ 89%, $T_{1/2}$=67.7 minutes) for imaging various rapidly changing processes (proliferation, apoptosis, angiogenesis) and targets (growth hormones, myocardial and pulmonary perfusion, inflammation and infection), and to some extent, to newer, more reliable production and labeling methods [Ref. 1-5]. Gallium-68 labeled somatostatin analogs have already shown their superiority over the existing agent $^{111}$In-DTPA-octreotide through enhanced sensitivity, specificity, accuracy and cost effectiveness for the diagnosis of patients with neuroendocrine tumors [Ref. 1, 6-9].

The clinical promise of $^{68}$Ga-labeled radiopharmaceuticals clearly warrants growth of the supply of $^{68}$Ga to meet the increasing demand in various nuclear medicine facilities. Presently, $^{68}$Ga can be produced by two different approaches, (1) solid targetry [Ref. 10,11] and (2) the $^{68}$Ge/$^{68}$Ga generator [Ref. 12]. The former requires high capital cost and expertise and specialized cyclotron facilities that accommodate solid targets, whereas, the latter is more broadly accessible in nuclear medicine facilities not equipped with an on-site cyclotron. The simplicity and lower capital cost of the $^{68}$Ge/$^{68}$Ga generator have made it more popular among the nuclear medicine facilities with relatively lower number of requirements for $^{68}$Ga labeled doses [Ref. 1, 12]. However, the breakthrough of trace quantities of the long-lived $^{68}$Ge parent isotope ($t_{1/2}$=271 days) into the eluted $^{68}$Ga remains a concern [Ref. 13]. Furthermore, with increasing applicability of $^{68}$Ga-labeled radiopharmaceuticals, one can foresee a need for alternative production methods to meet the increasing demand especially for the relatively busy nuclear medicine centers having an on-site cyclotron. There have been previous attempts to produce $^{68}$Ga using a cyclotron, initially employing a solid target method using $^{68}$Zn electrodeposition on a copper substrate [Ref. 10, 14] and more recently using a solution target containing an enriched $^{68}$ZnCl$_2$ solution [Ref. 15]. The solid target methods require a lengthy separation step, which is not optimal for short-lived isotopes like $^{68}$Ga, as well as expensive solid target infrastructure.

The production of $^{68}$Ga from a cyclotron using a liquid target method has been reported [Ref. 16]. However, due to the longer processing time, use of caustic acid HBr, use of organic solvents, and the large quantity of eluent used, this method may not be optimal for use in routine production and application of $^{68}$Ga.

Thus, there is a need in the art for improved methods and systems for rapid isolation of cyclotron produced radionuclides, such as $^{68}$Ga.

SUMMARY OF THE INVENTION $^{68}$Ga ($T_{1/2}$ 67.7 min) is a positron emission tomography (PET) isotope and is used to label peptides, proteins and small molecules for diagnostic PET imaging. $^{68}$Ga can be produced using a low energy cyclotron employing solid or liquid target methods. The processing of $^{68}$Ga produced in a cyclotron includes separation of $^{68}$Ga from the parent isotope $^{68}$Zn and other isotopes ($^{13}$N, $^{11}$C, $^{18}$F)) which may be formed during isotope production. Due to the 67.7 minute half-life of $^{68}$Ga, it is critical to have a simple and efficient processing method in order to minimize the loss of radioactivity by decay. The present disclosure provides a method for the separation of Gallium-68 from the parent Zinc-68 that reduces processing time and requires a smaller volume of final eluent. In one version of the invention, efficient trapping on a small volume of hydroxamate resin facilitates the reduction of final elution volumes to provide more concentrated solutions of Ga-68 for radiolabeling. In another version of the invention, more economical production of $^{68}$Ga from a cyclotron is achieved by efficient recycling of the parent isotope $^{68}$Zn using a method of recycling of $^{68}$Zn according to the present disclosure.

$^{67}$Ga may be used for SPECT imaging and/or therapeutic applications. One method of production of $^{67}$Ga requires separation of $^{67}$Ga from nonradioactive zinc cations.

In one aspect, this disclosure provides a method for producing a solution including a radionuclide. In the method, a target solution is bombarded with protons to produce a solution including a radionuclide, wherein the radionuclide is $^{68}$Ga. The solution including the radionuclide is passed through a column including a sorbent to adsorb the radionuclide on the sorbent, wherein the sorbent comprises a hydroxamate resin, and the radionuclide is eluted off the sorbent.

In another aspect, the disclosure provides a method for producing a solution including a radionuclide. In the method, a target solution including zinc cations is bombarded with protons to produce a solution including a radionuclide. The solution including the radionuclide is passed through a first column including a first sorbent to adsorb the radionuclide on the first sorbent, and the zinc cations are recovered from a recovery solution that has passed through the first column by passing the recovery solution through a second column including a second sorbent comprising a cation exchange resin.

In yet another aspect, the disclosure provides a method for producing a solution including a radionuclide. In the method, a solid target is bombarded with protons to produce a solid radionuclide, wherein the radionuclide is $^{68}$Ga. A solution including the radionuclide is created from the solid radionuclide. The solution including the radionuclide is then passed through a column including a sorbent to adsorb the radionuclide on the sorbent wherein the sorbent comprises a hydroxamate resin. The radionuclide is then eluted off the sorbent.

The foregoing and other aspects and advantages of the invention will appear from the following description. In the description, reference is made to the accompanying drawings that form a part hereof, and in which there is shown by way of illustration certain embodiments of the invention. Such embodiments do not necessarily represent the full scope of the invention, however, and reference is made therefore to the claims and herein for interpreting the scope of the invention.

BRIEF DESCRIPTION OF THE DRAWINGS

FIG. 1 is a schematic of an automated system for the separation of $^{68}$Ga radioisotope from a cyclotron produced solution including $^{68}$Ga.

DETAILED DESCRIPTION OF THE INVENTION

In one embodiment, the present disclosure provides a method for producing a solution including a radionuclide comprising the bombardment of a target solution with protons to produce a solution including a radionuclide, wherein the radionuclide is $^{68}$Ga; the passing of the solution including the radionuclide through a column including a sorbent to adsorb the radionuclide on the sorbent; and the elution of the radionuclide off the sorbent, wherein the sorbent comprises a hydroxamate resin. In one form, the target solution may comprise $^{68}$Zn-enriched zinc nitrate. The method may further comprise the elution of the radionuclide off the sorbent using hydrochloric acid, wherein an amount of eluent of 5 milliliters or less can be used. This method may take 30 minutes or less.

The method may further comprise adjusting pH of the solution including the radionuclide before passing the solution including the radionuclide through the column. In one version, these adjustments of the pH may comprise a dilution of the solution with water. The volume of water for dilution may range from 10 to 50 milliliters. In another version, the adjusting of the pH may comprise an addition of an organic or inorganic base to the solution. In this other version, the base may form a water soluble product with $^{68}$Ga and $^{68}$Zn. In one form of this other version, the base is sodium bicarbonate. The pH of the solution including the radionuclide before passing the solution including the radionuclide through the column may be between 5 and 7, preferably in a range of 5.5 to 6.5.

In this first embodiment, at least one of the steps of the method may be completed by an automated process using a remotely controlled radiochemistry module for processing in a hot cell as depicted in FIG. 1. The yield of the radionuclide from the solution including the radionuclide may be greater than 80% by radioactivity, or greater than 85% by radioactivity, or greater than 90% by radioactivity, or greater than 95% by radioactivity. In another form, the hydroxamate resin may comprise hydroxamate groups bonded to a backbone comprising a material selected from the group consisting of silica, polymer coated silica, polyacrylate, and polystyrene. In one non-limiting form, the hydroxamate resin comprises hydroxamate groups bonded to a backbone comprising an acrylic acid/acrylamide coated silica having a diol bonded phase. The hydroxamate resin may have a particle size in a range of 10 to 100 microns, or in a range of 20 to 70 microns, or in a range of 30 to 60 microns. In one non-limiting form, the hydroxamate resin has a particle size in a range of 37 to 55 microns.

In a second embodiment, the present disclosure provides a method for producing a solution including a radionuclide comprising the bombardment of a target solution including zinc cations with protons to produce a solution including a radionuclide; the passing of the solution including the radionuclide through a first column including a first sorbent to adsorb the radionuclide on the first sorbent; and the recovery of zinc cations from a recovery solution that has passed through the first column by passing the recovery solution through a second column including a second sorbent comprising a cation exchange resin. In one form, the method may comprise adjusting the pH of the recovery solution before passing the recovery solution through the second column. A beneficial pH range for the recovery solution before passing the recovery solution through the second column is a pH in a range of 3 to 7, or 4 to 6, or 4.5 to 5.5.

The first sorbent may be a hydroxamate resin comprising hydroxamate groups bonded to a backbone comprising a material selected from the group consisting of silica, polymer coated silica, polyacrylate, and polystyrene. In one non-limiting form, the hydroxamate resin comprises hydroxamate groups bonded to a backbone comprising an acrylic acid/acrylamide coated silica having a diol bonded phase. The hydroxamate resin may have a particle size in a range of 10 to 100 microns, or in a range of 20 to 70 microns, or in a range of 30 to 60 microns. In one non-limiting form, the hydroxamate resin has a particle size in a range of 37 to 55 microns. The second sorbent may comprise a polymeric resin having sulfonic acid groups. The second sorbent may be a polystyrene-divinylbenzene sulfonic acid such as that sold under the tradename AG® 50W-X8. The second sorbent may be a styrene-divinylbenzene co-polymer containing iminodiacetic acid groups such as that sold under the tradename Chelex® 100.

The method may further comprise washing the second column with deionized water before passing the recovery solution through the second column. The method may also comprise pushing air through the second column before passing the recovery solution through the second column. In yet another form, the target solution may comprise $^{68}$Zn-enriched zinc nitrate. The recovery of the zinc cations from the second column may be 90% or greater based on weight of the zinc cations in the target solution, or 93% or greater based on weight of the zinc cations in the target solution, or 95% or greater based on weight of the zinc cations in the target solution, or 98% or greater based on weight of the zinc cations in the target solution. In this second embodiment, at least one of the steps of the method may be completed by an automated process.

In a third embodiment, the present disclosure provides a method for producing a solution including a radionuclide comprising the bombardment of a solid target with protons to produce a solid radionuclide, wherein the radionuclide is $^{68}$Ga; the creation of a solution including the radionuclide from the solid radionuclide; the passing of the solution including the radionuclide through a column including a sorbent to adsorb the radionuclide on the sorbent; and the elution of the radionuclide off the sorbent, wherein the sorbent comprises a hydroxamate resin. In one form, the target solution may comprise $^{68}$Zn-enriched zinc nitrate. The method may further comprise the elution of the radionuclide off the sorbent using hydrochloric acid, wherein an amount of eluent of 5 milliliters or less can be used. This method may take 30 minutes or less.

The method may further comprise adjusting pH of the solution including the radionuclide before passing the solution including the radionuclide through the column. In one version, these adjustments of the pH may comprise a dilution of the solution with water. The volume of water for dilution may range from 10 to 50 milliliters. In another version, the adjusting of the pH may comprise an addition of an organic or inorganic base to the solution. In this other version, the base may form a water soluble product with $^{68}$Ga and $^{68}$Zn. In one form of this other version, the base is sodium bicarbonate. The pH of the solution including the radionuclide before passing the solution including the radionuclide through the column may be between 5 and 7, preferably in a range of 5.5 to 6.5.

In this third embodiment, at least one of the steps of the method may be completed by an automated process using a remotely controlled radiochemistry module for processing in a hot cell as depicted in FIG. 1. The yield of the radionuclide from the solution including the radionuclide may be greater than 80% by radioactivity, or greater than 85% by radioactivity, or greater than 90% by radioactivity, or greater than 95% by radioactivity. In another form, the hydroxamate resin may comprise hydroxamate groups bonded to a backbone comprising a material selected from the group consisting of silica, polymer coated silica, polyacrylate, and polystyrene. In one non-limiting form, the hydroxamate resin comprises hydroxamate groups bonded to a backbone comprising an acrylic acid/acrylamide coated silica having a diol bonded phase. The hydroxamate resin may have a particle size in a range of 10 to 100 microns, or in a range of 20 to 70 microns, or in a range of 30 to 60 microns. In one non-limiting form, the hydroxamate resin has a particle size in a range of 37 to 55 microns.

EXAMPLES

The following Examples are provided in order to demonstrate and further illustrate certain embodiments and aspects of the present invention and are not to be construed as limiting the scope of the invention.

Example 1

Introduction to Example 1

Hydroxamate mediated separation of Ga-68 from Zn-68 reduces processing time and provides a smaller volume of final eluent. Without limiting the present disclosure to a particular theory, it is contemplated that because Ga$^{3+}$ forms a hard Lewis acid in solution that it should form stable complexes with hard Lewis base groups, e.g., N, O groups of hydroxamate. In contrast, zinc forms a borderline Lewis acid, which has less of a chemical affinity for the hydroxamate resin. Efficient trapping on a small volume of hydroxamate resin should also facilitate the reduction of final elution volumes to provide more concentrated solutions of Ga-68 for radiolabeling. Experiments were performed according to the following procedure.

Materials and Methods

Chemicals

Zn-68 (99.23%) enriched metal was purchased from Cambridge Isotopes Laboratory (Tewksbury, Mass.). Hydrochloric acid (34-37% as HCl) and nitric acid (67-70% as HNO$_3$) both trace metals basis were purchased from Fisher Scientific (Suwanee, Ga.). AG-50W-X8 (polystyrene-divinylbenzene sulfonic acid resin, 200-400 mesh, hydrogen form) resin was purchased from Bio-Rad (Hercules, Calif.). Accell Plus CM (300 Å, WAT 010740) cation exchange resin (acrylic acid/acrylamide coated silica having a diol bonded phase—particle size: 37-55 μm—pore size: 300 angstroms) was purchased from Waters Inc. (Milford, Mass.). The activity readings were measured using a CRC dose calibrator (#416 setting, CRC-55tPET, Capintec, Ramsey, N.J.).

Synthesis of Hydroxamate Resin

Synthesis of hydroxamate resin was performed using a method developed by Pandey et al. [see Ref. 17 which is hereby incorporated by reference in the present disclosure]. Briefly, the hydroxamate resin was synthesized by stirring Accell Plus CM resin (2.00 g), methyl chloroformate (2.0 mL, 25.8 mmol) and triethylamine (2.0 mL, 14.3 mmol) in anhydrous dichloromethane (30 mL) at 0° C. for 30 minutes and then at room temperature for additional 90 minutes. The temperature of the mixture was further lowered to 0° C. before addition of hydroxylamine hydrochloride (0.6 g, 8.63 mmol) and triethylamine (2.0 mL, 14.3 mmol). The resultant mixture was stirred at room temperature for an additional 15 hours. The solvent was removed under vacuum, and cold water was poured with constant stirring into the flask containing the functionalized resin. The resin was filtered, washed extensively with water, and dried under vacuum.

Hydroxamate resin can also be prepared on various types of backbone polymers/resins including but not limited to polystyrene, silica, polyacrylate, polymer coated with silica or any other organic/inorganic backbone materials. Furthermore, the high degree of hydroxamate functionalization on any back bone polymer with different mesh sizes (bead size) enhances the separation of Ga-68/67 from Zn-68.

Results and Discussion

Isolation of $^{68}$Ga

A solution including $^{68}$Ga was produced in a solution target via 30 minute proton irradiation (current=20 μA) of a solution of 1.7 M $^{68}$Zn-zinc nitrate (99.23% isotopic enrichment) in 0.2 N nitric acid using a method developed by Pandey et al. [see Ref. 16 which is hereby incorporated by reference in the present disclosure]. A column loaded with 100 mg of the hydroxamate resin as synthesized above was pre-washed with 1 mL of acetonitrile and 10 mL of water. After irradiation, the contents of the cyclotron target was delivered to a collection vial pre-loaded with 25 mL of 20 mM NaHCO$_3$. The pH of the resultant solution (after addition of acidic target solution) was found to be in the range 5.5-6.5 for effective trapping of $^{68}$Ga on the hydroxamate resin. The neutralized target solution was passed through the hydroxamate resin to trap $^{68}$Ga, while allowing $^{68}$Zn and shorter lived isotopes $^{13}$N, $^{11}$C to pass through. Further rinsing of the parent $^{68}$Zn from the column was performed using 50 mL of water (pH 5.5). All $^{68}$Zn containing fractions were collected in a recovery vial for recycling of the parent $^{68}$Zn isotope. Finally, $^{68}$Ga was eluted from the hydroxamate resin with 2 mL 2 M hydrochloric acid and collected in a product vial for subsequent labeling.

This process was automated using a remotely controlled radiochemistry module for processing in a hot cell as depicted in FIG. 1. A programmable microprocessor-based controller was in electrical communication with valves V of the system 100 of FIG. 1 to open and close the valves when necessary to transfer fluids in the fluid lines L of FIG. 1. Suitable timing of valve opening and closing was programmed in the controller. The processing was achieved in approximately 20 minutes with greater than 80% yield, decay corrected to start of processing.

Using the radiochemistry module as depicted in FIG. 1 with the hydroxamate resin as synthesized above, processing times of 20-25 minutes can provide a trapping efficiency of 70-90%, an elution efficiency of 95-98%, and an overall efficiency of 70-90%.

An analysis of metal impurities in the $^{68}$Ga product was as follows: Ga: 0.3±0.1 µg, Cu: 10.2±7.3 µg, Zn: 33.3±21 µg, and Fe: 31.9±26.2 µg for an ICP-MS analysis of ten different batches.

Recycling of $^{68}$Zn

Economical production of $^{68}$Ga from a cyclotron requires efficient recycling of the parent isotope $^{68}$Zn. A method of recycling of $^{68}$Zn was also developed. The pH of the recovered $^{68}$Zn solution (above) was adjusted to pH=5.0 by addition of nitric acid. The resultant $^{68}$Zn solution was passed through a column containing 1.5 grams of cation exchange resin (Bio-Rad AG-50W-X8, 200-400 mesh, hydrogen form). Prior to use, the cation exchange resin was washed with 60 mL of water followed by 20 mL of air. $^{68}$Zn was trapped on the cation exchange resin. The resin was washed with an additional 10-15 mL of water (pH 5.0-5.5) with minimal loss of $^{68}$Zn. Finally, $^{68}$Zn was eluted from the resin with 15 mL of 8 M HNO$_3$. The recovered $^{68}$Zn nitrate solution was dried under vacuum for subsequent use to produce $^{68}$Ga. $^{68}$Zn recovery was found to exceed 98%. ICP-MS analysis of the recovered $^{68}$Zn showed presence of insignificant quantities of metal ion impurities, such as sodium.

Thus, an improved method of Ga-68 purification and $^{68}$Zn recovery have been achieved. The developed method further simplifies a solution target approach of $^{68}$Ga production.

Example 2

Hydroxamate mediated separation of $^{68}$Ga from $^{68}$Zn is facilitated by a pH adjustment of the target solution. As will be detailed below, the separation of $^{68}$Ga from $^{68}$Zn has been accomplished in two different ways.

Non-Base Mediated pH Adjustment

First, a non-base mediated pH adjustment was performed through dilution of post-irradiated $^{68}$Ga target solution with water. Various quantities of water were used to achieve different pH values before trapping $^{68}$Ga on hydroxamate resin. The amount of water used to adjust pH increases with increasing strength of the nitric acid and/or molarity of the $^{68}$Zn solutions used in target irradiation. Results are shown below in Table 1.

TABLE 1

Summary of the Non-Base Mediated Purification of Ga-68 from the Zn-68

| | Run # | | | | |
|---|---|---|---|---|---|
| | 1 | 2 | 3 | 4 | 5 |
| Solution composition | 0.5M salt in 0.8N HNO$_3$ | | | | |
| Irradiation condition | 45 µA, 30 min | | | | 45 µA, 60 min |
| Hydroxamate (mg) (modified) | 700 mg | 700 mg | 250 mg | 250 mg | 750 mg |
| Amount of water used (mL) | 15.0 mL | | | | |
| Turbidity/precipitate | No | No | No | No | No |
| % of activity as Product | 9.5% | 18.9% | 14.2% | 9.6% | 23.1% |
| % of activity in Zn-68 recovery vial | 88.5% | 76.9% | 84.3% | 88.3% | 63.4% |
| % of activity retained on hydroxamate | 2.0% | 4.1% | 1.3% | 2.1% | 13.5% |

Base Mediated pH Adjustment

Various organic and inorganic bases were employed to achieve a desired pH of the target solution before trapping $^{68}$Ga on hydroxamate resin. Herein, we demonstrated the use of sodium bicarbonate to achieve the desired pH. The amount of base (bicarbonate or appropriate organic/inorganic base) used to adjust pH is dependent upon the strength of the nitric acid and molarity of the $^{68}$Zn solutions used in target irradiation. Higher concentrations of nitric acid and $^{68}$Zn nitrate salt required higher strength of base solution to adjust the pH to the desired level (pH between 5.5 and 6.5). The selection of base also depends upon the solubility of the resultant species formed after neutralization. If the resultant species formed are insoluble in aqueous solution, then they cannot be used for automated separation of $^{68}$Ga from parent $^{68}$Zn. For example, if the acidic post-irradiation target solution is neutralized with sodium hydroxide, then the resultant species formed will be zinc hydroxide and gallium hydroxide. The hydroxides of Ga and Zn are poorly soluble in water and therefore, would not be appropriate. Similar rationale can be applied to other organic/inorganic bases before their use in this hydroxamate based method of separation of $^{68}$Ga from $^{68}$Zn. Sodium bicarbonate was chosen because it yields sodium nitrate, carbonic acid and zinc bicarbonate after neutralization and allows $^{68}$Zn nitrate to be obtained effectively during the recycling process. Results are shown below in Table 2.

TABLE 2

Summary of the Base Mediated Purification of Ga-68 from the Zn-68

| | Run # | | | | | | | | |
|---|---|---|---|---|---|---|---|---|---|
| | 1 | 2 | 3 | 4 | 5 | 6 | 7 | 8 | 9 |
| Solution composition | 0.5M salt in 0.8N HNO$_3$ | 1.0M salt in 0.8N HNO$_3$ | | | | 1.0M salt in 1.25N HNO3 | 1.0M salt in 1.5N HNO$_3$ | | |
| Irradiation condition | 30 µA, 60 min | 40 µA 60 min | 20 µA, 60 min | 30 µA, 60 min | 40 µA, 60 min | 30 µA, 60 min | 40 µA 60 min | 30 µA, 60 min | |
| Hydroxamate (mg) (modified) | | | | | 100 mg | | | | |
| pH (after neutralization) | 6.0 | 5.86 | 5.96 | 6 | 5.9 | 5.92 | 5.96 | 5.94 | 5.95 |
| 0•13N NaHCO$_3$ (mL) | 14.3 | | | 12.9 | | 21.0 | 25.4 | 25.4 | |
| Turbidity/ precipitate | No | No | No | No | No | No | No | no | no |
| % of activity as Product | 69.34 | 68.53 | 82.49 | 86.10 | 71.26 | 89.80 | 73.94 | 76.18 | 80.49 |
| % of activity in Zn-68 recovery vial | 28.50 | 29.21 | 13.65 | 10.07 | 27.26 | 7.83 | 19.82 | 21.88 | 5.06 |
| % of activity retained on hydroxamate | 2.16 | 2.26 | 3.86 | 3.83 | 1.48 | 2.37 | 6.25 | 1.94 | 14.44 |

Note:
1. Activity lost in the lines and collection flask have not been included in the calculation.
2. These runs are processed after 2.5 to 3 hours post irradiation.

Recycling of $^{68}$Zn

Recycling of recovered $^{68}$Zn(NO$_3$)$_2$ was performed on a cation exchange column using 1.5-1.6 grams of AG 50W-X8 resin. Prior to the recycling of $^{68}$Zn, an AG 50W-X8 resin column was washed with 60 mL of deionized water dropwise followed by 20 mL of air. Before passing the recovery solution through the column, the pH of the recycling solution was adjusted to ≤5 using dilute nitric acid, if needed. After passing the recovery solution through the column, 20 mL of air was also pushed through. The column was washed with 10 mL of deionized water, followed by 20 mL of air. $^{68}$Zn was eluted with 15 mL of 8N HNO$_3$ into a fresh vial, and followed by 20 mL of air. The obtained $^{68}$Zn nitrate solution was concentrated on a rotary evaporator. The column was regenerated by passing an additional 2 mL of concentrated HNO$_3$ (15.9 N). To reuse this column, a step of activation with 60 mL of deionized water and a step of 20 mL of air were performed. Results are shown below in Tables 3-4.

TABLE 3

% of Zn-68 nitrate recovered in comparison with known starting mass of zinc nitrate (Batch-1)

| Recycling process | Molarity of Solution (M) | Mass of Zinc Nitrate Hexahydrate Used (g) | Mass Found After Concentration (g) | Efficiency |
|---|---|---|---|---|
| 1 | 0.5 | 0.330 | 0.293 | |
| 2 | 0.5 | 0.330 | 0.354 | |
| 3 | 0.5 | 0.330 | 0.403 | |
| 4 | 1 | 0.660 | 0.571 | |
| 5 | 1 | 0.660 | 0.531 | |
| Total | | 2.310 | 2.152 | 93.2% |

TABLE 4

% of Zn-68 nitrate recovered in comparison with known starting mass of zinc nitrate (Batch-2).

| Recycling process | Molarity of Solution (M) | Mass of Zinc Nitrate Hexahydrate Used (g) | Mass Found After Concentration (g) | Efficiency |
|---|---|---|---|---|
| 1 | 1 | 0.660 | 0.629 | |
| 2 | 1 | 0.660 | 0.737 | |
| 3 | 1 | 0.660 | 0.470 | |
| 4 | 1 | 0.660 | 0.590 | |
| Total | | 2.640 | 2.426 | 91.9% |

REFERENCES

[1] Velikyan I., Prospective of $^{68}$Ga-Radiopharmaceutical Development. *Theranostics* 2014; 4: 47-80.
[2] Banerjee S R, Pomper M G., Clinical applications of Gallium-68. *Appl Radiat Isot* 2013; 76: 2-13.
[3] Zimmerman B E., Current status and future needs for standards of radionuclides used in positron emission tomography. *Appl Radiat Isot* 2013; 76: 31-37.
[4] Smith D L, Breeman W A P, Sims-Mourtada J., The untapped potential of Gallium 68-PET: The next wave of $^{68}$Ga-agents. *Appl Radiat Isot* 2013; 76: 14-23.
[5] Baum R P, Kulkarni H R., Theranostics: from molecular imaging using Ga-68 labeled tracers and PET/CT to personalized radionuclide therapy—the Bad Berka experience. *Theranostics* 2012; 2: 437-47.
[6] Öberg K., Gallium-68 somatostatin receptor PET/CT: Is it time to replace $^{111}$Indium DTPA octreotide for patients with neuroendocrine tumors? *Endocrine* 2012; 42: 3-4.
[7] Schreiter N F, Brenner W, Nogami M, Buchert R, Huppertz A, Pape U F, Prasad V, Hamm B, Maurer M H., Cost comparison of $^{111}$In-DTPA-octreotide scintigraphy and $^{68}$Ga-DOTATOC PET/CT for staging enteropancreatic neuroendocrine tumours. *Eur J Nucl Med Mol Imaging* 2012; 39: 72-82.

[8] Hofman M S, Kong G, Neels O C, Eu P, Hong E, Hicks R J., High management impact of Ga-68 DOTATATE (GaTate) PET/CT for imaging neuro-endocrine and other somatostatin expressing tumours. *J Med Imaging Radiat Oncol* 2012; 56: 40-7.

[9] Jacobsson H, Larsson P, Jonsson C, Jussing E, Gryback P., Normal uptake of $^{68}$Ga-DOTA-TOC by the pancreas uncinate process mimicking malignancy at somatostatin receptor PET. *Clin Nucl Med* 2012; 37: 362-5.

[10] Engle J W, Lopez-Rodriguez V, Gaspar-Carcamo R E, Valdovinos H F, Valle-Gonzalez M, Trejo-Ballado M, Severin G W, Barnhart T E, Nickles R J. Avila-Rodriguez M A., Very high specific activity $^{66/68}$Ga from zinc targets for PET. *Appl Radiat Isot* 2012; 70: 1792-1796.

[11] Sadeghi M, Kakavand T, Rajabifar S, Mokhtari L, Nezhad A R., Cyclotron production of $^{68}$Ga via proton-induced reaction on $^{68}$Zn target. *Nukleonika* 2009; 54: 25-28.

[12] Rosch F., Past, present and future of $^{68}$Ge/$^{68}$Ga generators. *Appl Radiat Isot* 2013; 76: 24-30.

[13] Belosi F, Cicoria G, Lodi F, Malizia C, Fanti S, Boschi S, Marengo M., Generator breakthrough and radionuclidic purification in automated synthesis of $^{68}$Ga-DOTANOC. *Curr Radiopharm* 2013, 6: 72-7.

[14] Sadeghi M, Kakavand T, Mokhtari L, Gholamzadeh Z., Determination of $^{68}$Ga production parameters by different reactions using ALICE and TALYS codes. *Pramana J Phys* 2009; 72: 335-341.

[15] Jensen M, Clark J., Direct production of Ga-68 from proton bombardment of concentrated aqueous solutions of [Zn-68] zinc chloride. *Proceedings of 13th International Workshop on Targetry and Target Chemistry* 2011; 288-292.

[16] M. K. Pandey, J. F. Byrne, A. Jiang, A. B. Packard, T. R. DeGrado. *Am. J. Nucl. Med. Mol. Imaging.* 4, pp. 303-310, 2014.

[17] M. K. Pandey, A. Bansal, H. P. Engelbrecht, J. F. Byrne, A. B. Packard, T. R. DeGrado. *Nucl. Med. Biol.* 43(1), pp. 97-100, 2016

The citation of any document or reference is not to be construed as an admission that it is prior art with respect to the present invention.

Thus, the present invention provides improved methods and systems for rapid isolation of cyclotron produced radionuclides, such as $^{68}$Ga. The methods of processing $^{68}$Ga and recycling of $^{68}$Zn offer an economical alternative to $^{68}$Ge/$^{68}$Ga generators.

Although the invention has been described with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method for producing a solution including a radionuclide, the method comprising:
   (a) bombarding a target solution with protons to produce a solution including a radionuclide, wherein the radionuclide is $^{68}$Ga;
   (b) passing the solution including the radionuclide through a column including a sorbent to adsorb the radionuclide on the sorbent; and
   (c) eluting the radionuclide off the sorbent,
   wherein the sorbent comprises a hydroxamate resin, and
   wherein pH of the solution including the radionuclide before passing the solution including the radionuclide through the column is between 5 and 7.

2. The method of claim 1, wherein the target solution comprises $^{68}$Zn-enriched zinc nitrate.

3. The method of claim 1, wherein step (c) comprises eluting the radionuclide off the sorbent using hydrochloric acid.

4. The method of claim 1,
   wherein step (c) comprises eluting the radionuclide off the sorbent with an amount of eluent of 5 milliliters or less, and
   wherein the method takes 30 minutes or less.

5. The method of claim 1, wherein step (b) comprises adjusting pH of the solution including the radionuclide before passing the solution including the radionuclide through the column.

6. The method of claim 5, wherein the adjusting of the pH comprises a dilution with water.

7. The method of claim 5, wherein the adjusting of the pH comprises an addition of a base, and wherein the base forms a soluble product with $^{68}$Ga and $^{68}$Zn.

8. The method of claim 1, wherein yield of the radionuclide from the solution including the radionuclide is greater than 80% by radioactivity.

9. The method of claim 1, wherein the hydroxamate resin comprises hydroxamate groups bonded to a backbone comprising a material selected from the group consisting of silica, polymer coated silica, polyacrylate, and polystyrene, and wherein the hydroxamate resin has a particle size in a range of 10 to 100 microns.

10. The method of claim 1, wherein the hydroxamate resin comprises hydroxamate groups bonded to a backbone comprising an acrylic acid/acrylamide coated silica having a diol bonded phase.

11. A method for producing a solution including a radionuclide, the method comprising:
    (a) bombarding a solid target with protons to produce a solid radionuclide, wherein the radionuclide is $^{68}$Ga;
    (b) creating a solution including the radionuclide from the solid radionuclide;
    (c) passing the solution including the radionuclide through a column including a sorbent to adsorb the radionuclide on the sorbent; and
    (d) eluting the radionuclide off the sorbent,
    wherein the sorbent comprises a hydroxamate resin, and
    wherein pH of the solution including the radionuclide before passing the solution including the radionuclide through the column is between 5 and 7.

12. The method of claim 11, wherein the solution comprises $^{68}$Zn-enriched zinc nitrate.

13. The method of claim 11, wherein step (c) comprises eluting the radionuclide off the sorbent using hydrochloric acid.

14. The method of claim 11,
    wherein step (c) comprises eluting the radionuclide off the sorbent with an amount of eluent of 5 milliliters or less, and
    wherein the method takes 30 minutes or less.

15. The method of claim 11, wherein step (b) comprises adjusting pH of the solution including the radionuclide before passing the solution including the radionuclide through the column.

16. The method of claim 15, wherein the adjusting of the pH comprises a dilution.

17. The method of claim 15, wherein the adjusting of the pH comprises an addition of a base, and wherein the base forms a soluble product with $^{68}$Ga and $^{68}$Zn.

18. The method of claim 11, wherein yield of the radionuclide from the solution including the radionuclide is greater than 80%.

19. The method of claim 11, wherein the hydroxamate resin comprises hydroxamate groups bonded to a backbone comprising a material selected from the group consisting of silica, polymer coated silica, polyacrylate, and polystyrene, and wherein the hydroxamate resin has a particle size in a range of 10 to 100 microns.

20. The method of claim 11, wherein the hydroxamate resin comprises hydroxamate groups bonded to a backbone comprising an acrylic acid/acrylamide coated silica having a diol bonded phase.

* * * * *